US012590860B2

(12) United States Patent
Holman et al.

(10) Patent No.: US 12,590,860 B2
(45) Date of Patent: Mar. 31, 2026

(54) MONITORING SYSTEM, A METHOD FOR MONITORING, AND A ROOM

(71) Applicant: GEA Process Engineering NV, Wommelgem (BE)

(72) Inventors: James William Holman, Bonheiden (BE); Phillip Michael Gabb, Gloucester (GB)

(73) Assignee: GEA Process Engineering NV, Wommelgem (BE)

( * ) Notice: Subject to any disclaimer, the term of this patent is extended or adjusted under 35 U.S.C. 154(b) by 310 days.

(21) Appl. No.: 18/564,856

(22) PCT Filed: May 27, 2022

(86) PCT No.: PCT/EP2022/064411
§ 371 (c)(1),
(2) Date: Nov. 28, 2023

(87) PCT Pub. No.: WO2022/248667
PCT Pub. Date: Dec. 1, 2022

(65) Prior Publication Data
US 2024/0288331 A1     Aug. 29, 2024

(30) Foreign Application Priority Data
May 28, 2021     (EP) ..................................... 21176678

(51) Int. Cl.
G01M 3/22          (2006.01)
G01N 1/22          (2006.01)
(Continued)

(52) U.S. Cl.
CPC ............ G01M 3/22 (2013.01); G01N 1/2226 (2013.01); G01N 1/24 (2013.01); G01N 15/06 (2013.01); G01N 33/0036 (2013.01)

(58) Field of Classification Search
CPC ......... G01M 3/22; G01N 1/2226; G01N 1/24; G01N 15/06; G01N 33/0036; G01N 15/02
See application file for complete search history.

(56) References Cited

U.S. PATENT DOCUMENTS 10,016,340 B2     7/2018   Boeckx et al.
10,976,212 B2     4/2021   Kawasaki
(Continued)

FOREIGN PATENT DOCUMENTS

CN        107588908 A        1/2018
EP        3797276 A2         3/2021
(Continued)

*Primary Examiner* — Laura Martin
*Assistant Examiner* — Anthony W Megna Fuentes
(74) *Attorney, Agent, or Firm* — Flaster Greenberg P.C.

(57)          ABSTRACT

Disclosed is a monitoring system for monitoring performance of a contained system for processing pharmaceutical components, the contained system comprising one or more inlets for receiving one or more pharmaceutical components and one or more outlets, the monitoring system comprising a first sensor and a processing unit operationally connectable to the first sensor. Also disclosed is a method for monitoring performance of a contained system for processing pharmaceutical components and a room comprising a contained system and the monitoring system.

20 Claims, 6 Drawing Sheets

(51) Int. Cl.
    *G01N 1/24*         (2006.01)
    *G01N 15/02*       (2024.01)
    *G01N 15/06*       (2024.01)
    *G01N 33/00*       (2006.01)

(56)               References Cited

U.S. PATENT DOCUMENTS

| | | |
|---|---|---|
| 2012/0006186 A1 | 1/2012 | Hugus et al. |
| 2012/0014737 A1 | 1/2012 | Yoon |
| 2016/0061797 A1* | 3/2016 | Kocher .............. G01N 33/0073 |
| | | 702/24 |
| 2019/0265122 A1 | 8/2019 | Kawasaki |
| 2021/0010414 A1 | 1/2021 | Julien et al. |

FOREIGN PATENT DOCUMENTS

| | | |
|---|---|---|
| GB | 2064787 A | 6/1981 |
| JP | 2012525895 A | 10/2012 |
| JP | 2018080998 A | 5/2018 |
| WO | 2010128359 A1 | 11/2010 |
| WO | 2012125108 A1 | 9/2012 |

* cited by examiner

3

MONITORING SYSTEM, A METHOD FOR MONITORING, AND A ROOM

CROSS-REFERENCE TO RELATED APPLICATIONS

This application is the 371 National Stage of International Application No. PCT/EP2022/064411, filed May 27, 2022, which claims the benefit of European Patent Application No. 21176678.7, filed May 28, 2021 the disclosures of which are incorporated herein by reference in their entirety.

FIELD

The present disclosure relates to a monitoring system for monitoring performance of a contained system for processing pharmaceutical components. The present disclosure further relates to a method for monitoring performance of a contained system for processing pharmaceutical components and to a room comprising a contained system for processing pharmaceutical components and a monitoring system for monitoring performance of the contained system.

BACKGROUND

In processing pharmaceutical components, one or more components, such as ingredients, also referred to as excipients, or active pharmaceutical ingredients (APIs) are typically processed with the object of manufacturing another pharmaceutical component and/or a pharmaceutical product. Such one or more components are often input to a system for processing pharmaceutical components in the form of powders or granulates, which during the processing are typically processed, e.g. mixed and/or pressed to tablets.

However, the processing of such components, e.g. in powder form, often requires measures to be taken to reduce the risk for operators of the pharmaceutical system. For instance, when the pharmaceutical system processes the one or more components, some of these may be emitted into the air surrounding the pharmaceutical system. To prevent an operator from being exposed to these pharmaceutical components, the pharmaceutical system is often contained, so as to reduce the risk of components from escaping into the air surrounding the system.

Such containment capabilities should generally be evaluated to ensure that sufficient containment is established and that no leakage occurs in the pharmaceutical system. Typically, containment capabilities are determined based on checks before the manufacturing system is put in operation, for instance using a pressure decay test. In a typical pressure decay test, a negative pressure, often of around a couple of kPa, is applied inside the contained system and the rise time for the pressure to rise inside the contained system from a first value to a second value is measured. If the rise time for the pressure lies within a predefined range, the pharmaceutical system is considered to have sufficient containment and is then considered contained. If the rise time lies without the predefined range, the pharmaceutical system is considered not sufficiently and contained and a second test, such as a helium leak test, is then typically performed to find the breach.

Performing a pressure decay test is, however, complex and time-consuming. Moreover, the manufacturing system must be stopped from its processing of pharmaceutical components to perform the pressure decay test, which typically is to be performed with a few hours interval, thus causing regular downtime of the manufacturing system.

Thus, it remains a desire to provide an improved method and system for monitoring performance of the contained system.

SUMMARY

An object of the present invention is to address at least some of the above-mentioned drawbacks.

According to an aspect of the present disclosure, there is provided a monitoring system for monitoring performance of a contained system for processing pharmaceutical components, the contained system comprising one or more inlets for receiving one or more pharmaceutical components and one or more outlets, the monitoring system comprising a first sensor and a processing unit operationally connectable to the first sensor, wherein the first sensor is configured to be arranged outside of the contained system at a first point, and the first sensor is configured to repeatably provide to the processing unit a sensor signal indicative of a particle concentration in air outside the contained system, wherein the processing unit is configured to compare the sensor signal with an expected sensor signal, and wherein the processing unit, where the processing unit determines that the sensor signal is different from the expected sensor signal, is configured to output an output signal indicative of an air particle concentration being different than an expected air particle concentration.

The first sensor may be configured to repeatably provide to the processing unit a sensor signal indicative of a particle concentration of particles having a size larger than 0.1 micrometre in air outside the contained system.

Thereby, the monitoring system allows a determination of particles in air outside the contained system and thereby allows the monitoring system to determine containment capabilities and/or a containment breach, e.g. by detecting particles from the pharmaceutical components in the air outside the contained system. Moreover, by means of the first sensor, the monitoring system may further determine a particle concentration while the contained system is processing pharmaceutical components, thereby allowing for monitoring of containment capabilities of the contained system during the processing of pharmaceutical components. For instance, such monitoring may be carried out continuously during the processing, thereby allowing for a containment breach, i.e. insufficient containment capabilities, to be determined shortly after it occurs. This, again, allows for taking appropriate measures after the containment breach has occurred, thereby improving the safety for the operator(s).

By the processing unit comparing the sensor signal with the expected sensor signal and outputs a signal, where the sensor signal is different from the expected sensor signal, the monitoring system may determine if a leakage has occurred and alarm and/or take action, where a leakage has occurred. Thereby, the monitoring system may take an appropriate action, e.g. sound an alarm, shut down the contained system, interlock access to the contained system, and/or transmitting a message to one or more operators, when a leakage in the contained system is detected.

It has furthermore been realised that, by the first sensor being configured to be arranged outside the contained system, the first sensor and/or the monitoring system may be easily mounted on an existing contained system and may be retrofittable on the contained system without breaching the containment.

Additionally, by the first sensor being configured to be arranged at a first point outside the contained system, the monitoring system may detect a containment breach, i.e. a leakage, from a specific area of the contained system near the first point, thereby allowing the monitoring system to determine where in the contained system a leakage has occurred.

By the term "contained system" is herein to be understood that a system is to fulfil certain requirements to containment, i.e. that the system when functioning is at least dust tight. Correspondingly, a contained system may be a system which when functioning is configured to prevent that extensive amounts, such as detectable amounts and/or amounts over a certain threshold, of the one or more components are emitted from the contained system into the surroundings, such as into a room in which it is arranged. By "contained system" may herein be understood that the system is to have a containment capability of dust containment of up to 10 µg per m³. Correspondingly the contained system may be a system, which when functioning is configured to have a dust containment of up to 10 µg per m³.

It will be appreciated, throughout this text, that the term air particle concentration refers to the particle concentration in the air outside the contained system. The term air particle concentration, thus, refers to a concentration of particles in the air outside the system.

The particle concentration in the air outside the contained system and/or the air particle concentration may be a concentration of particles in the air, with the proviso that gas particles are excluded. Alternatively or additionally, the first sensor may be configured to repeatedly provide to the processing unit a sensor signal indicative of a particle concentration of particles, which do not comprise gas particles, in the air.

The contained system may be configured to be arranged in a room, such as a facility and/or room in accordance with Good Manufacturing process (GMP), and/or may be arranged in a GMP facility or GMP room.

One or more of the one or more components may be in the form of powder(s). The one or more inlets for receiving the one or more pharmaceutical components may be configured to receive the one or more pharmaceutical components in the form of powder(s) and/or granulate(s).

By the first sensor being configured to be arranged "outside" of the contained system is herein meant that the first sensor is configured to be arranged exteriorly of the containment. The term "outside" may thus refer to a room, in which the contained system is arranged, and/or to the surroundings of the contained system, such as an area which is accessible by an operator.

In some embodiments, the one or more inlets and/or the outlet May define an interface between the contained system and the outside thereof.

By the term "air outside the contained system" is, hence, to be understood air which is not enclosed in the contained system. Thus, the air outside the contained system may be air surrounding the contained system and/or air in a room surrounding the contained system. Alternatively or additionally, the air outside the contained system may be air in fluid connection with air, which can be breathed in by an operator.

Throughout this text, it will be appreciated that a fluid connection between two elements may be a connection, which allows a fluid, such as air, to flow, such as flow uninterruptedly, from one element to another, for instance during normal operation of the contained system. As an example, two elements arranged within the same enclosed volume, such as a room, may be in fluid connection, and/or two elements connected by a tube, through which a fluid, such as air, can flow, may be in fluid connection.

The monitoring system for monitoring performance of a contained system for processing pharmaceutical products may be a monitoring system configured to monitor performance of a contained system for processing pharmaceutical products.

The contained system for processing pharmaceutical products may further to the at least one inlet and at least one outlet comprise a further element, such as one or more containers for the one or more pharmaceutical components. Any one of the one or more inlets may be connected to any one of the one or more containers, potentially so that a pharmaceutical component can be transferred into the one or more containers via one or more of the one or more inlets.

Alternatively or additionally, the contained system may comprise a first and a second module connected at an interface. Potentially, each of the first and second module may be or comprise a container, such as a, potentially docked, intermediate bulk container (IBC), a mixer for mixing the one or more pharmaceutical components, and/or a tablet press for pressing tablets. The tablet press may be for pressing tablets from some or all of the one or more pharmaceutical components or a mix thereof. The outlet of the contained system may be an outlet of the mixer or an outlet of a tablet press.

The contained system may comprise a plurality of interfaces between elements and/or modules thereof, such as between an inlet and an outlet thereof. For instance, where the contained system comprises a mixer, the contained system may comprise at least one interface between the mixer and any of the one or more inlets. Similarly, where the contained system comprises a tablet press, as an example, the contained system may comprise an interface between the one or more inlets and the tablet press, between the mixer and the tablet press, and/or between the tablet press and the outlet. Alternatively or additionally, the contained system may comprise a plurality of valves.

Each of the one or more pharmaceutical components may comprise or may be an ingredient, an active pharmaceutical ingredient (API), and/or an excipient.

A sensor signal indicative of the particle concentration may be an analogue signal, a time-discrete signal, or a digital signal. The sensor signal may comprise a sensor reading, such an analogue signal or a digital signal, of light scattered on one or more particles. Alternatively or additionally, the sensor signal may comprise a sensor reading, such as a digital number, of a count of particles and/or a sensor reading, such as a digital number, of a concentration of particles in a predetermined volume of air.

The first sensor may be an optical sensor, such as a light-scattering sensor, configured to measure particle concentration in air.

The first sensor may comprise a sensor processing unit configured to output the sensor signal indicative of the particle concentration. The sensor processing unit may be configured to output an analogue or digital sensor signal indicative of the particle concentration. The sensor processing unit may a central processing unit (CPU), a micro controller unit (MCU), a field-programmable gate array (FPGA), or the like.

The first sensor may comprise a data interface, such as a wired data interface or a wireless data interface for outputting the sensor signal to the processing unit.

The processing unit of the monitoring system may be a CPU, a MCU, a FPGA, or the like. By the processing unit being in operable connection with the first sensor may here be understood that the processing unit is configured to receive the first sensor signal from the first sensor. The processing unit may be configured to receive a respective sensor signal from any potential other sensor of the monitoring system. Where the sensor comprises a sensor processing unit, the processing unit may be configured to be in operable connection with the sensor processing unit.

The processing unit may be configured to be arranged outside the contained system, such as in a room surrounding the contained system or outside a room surrounding the contained system. Alternatively, the processing unit may be configured to be arranged in the contained system.

The sensor signal may directly specify the particle concentration e.g. the sensor signal may specify a count of particles in a predetermined volume of air. Alternatively or additionally, the first sensor signal may specify a particle count from which the particle concentration may be estimated e.g. using knowledge about the volume of air the first sensor has analysed.

The processing unit may be configured to determine a particle concentration in the air based at least in part on the first sensor signal.

In some embodiments, the first sensor is configured to be arranged in proximity to a first potential leakage zone of the contained system.

Thereby, a leakage and, thus, containment breach may be identified at an early stage, thereby allowing for action to be taken early to further reduce the risk for operator(s).

Any potential leakage zone, such as the first potential leakage zone, may comprise one or more potential leakage points. A potential leakage zone may be a zone, an area, and/or a point of the contained system, at which there is an increased risk of leakage and, thus, risk of containment breach. In some embodiments, a potential leakage zone is one of the one or more inlets or the one or more outlets. Alternatively or additionally, where the contained system comprises a first and a second module connected at an interface, a potential leakage zone may be an inlet, an outlet, and/or the interface. For instance, where the contained system comprises a mixer and/or a tablet press, a potential leakage zone may be any of the one or more inlets, any of the one or more outlets, an interface between a mixer and another element. Alternatively or additionally, a potential leakage zone may be a valve of the contained system. A potential leakage zone may comprise a plurality of potential leakage sub-zones, potentially each comprising a plurality of potential leakage points, and/or may comprise a plurality potential leakage points.

Additionally or alternatively, the first potential leakage zone may be selected from a list of potential leakage zones, such as a list comprising the potential leakage zones described above.

In some embodiments, the monitoring system further comprises a second sensor operationally connectable to the processing unit, wherein the second sensor is configured to be arranged outside of the contained system at a second point, and wherein the second sensor is configured to repeatedly provide to the processing unit a second sensor signal indicative of a particle concentration in air outside the contained system.

Thereby, the contained system may be monitored at multiple points, allowing for the monitoring system to aid in estimating or to estimate where in the contained system the leakage has occurred, potentially without requiring further testing.

The second sensor may comprise any of the features described above with respect to the first sensor and/or may be similar or identical to the first sensor.

In some embodiments, the second sensor is configured to be arranged in proximity with a second potential leakage zone. The second potential leakage zone may be a potential leakage zone as described above with respect to the first leakage zone. Alternatively or additionally, the second sensor may be configured to be arranged with a distance to the first sensor and in proximity with the first potential leakage zone.

The expected sensor signal may be indicative of an expected particle concentration in the air outside the contained system, such as the air around the first point, at which the first sensor is arranged. The expected sensor signal may represent a sensor signal as expected when the contained system performance is considered adequate, such as when the contained system has sufficient containment capabilities. The expected sensor signal may be based on the containment of the contained system. Alternatively or additionally, the expected sensor signal may represent and/or may be threshold value, wherein the processing unit of the monitoring system is configured to determine that a leakage has occurred and/or determine an insufficient performance of the contained system when the first sensor signal exceeds the threshold value. The threshold may be a, potentially predetermined, particle concentration threshold value. The threshold may, alternatively, be dynamically determined based on other inputs to the monitoring system e.g. based on inputs from a background or reference sensor.

Alternatively or additionally, the expected sensor signal may represent and/or may be a value range, wherein the processing unit of the monitoring system may be configured to determine that a leakage has occurred and/or determine an insufficient performance of the contained system when the first sensor signal is outside the value range. The value range may be a, potentially predetermined, particle concentration value range. The processing unit of the monitoring system may be configured to determine that a leakage has occurred and/or determine an insufficient performance of the contained system when the first sensor signal indicates a particle concentration outside the particle concentration value range.

In some embodiments, the processing unit may be configured to compare the second sensor signal with a second expected sensor signal. A second expected sensor signal may comprise some or all of the features described with respect to the expected sensor signal and/or be identical or similar thereto. As an example, the expected sensor signal and the second expected sensor signal may each represent a respective threshold value or value range. Alternatively or additionally, the processing unit may be configured to compare the second sensor signal with the expected sensor signal.

The output signal may be an analogue or digital output signal, such as a digital binary or Boolean signal. The output signal may be transmitted to a further device, such as an alarm, a locking device, a display, or the like.

In some embodiments, the processing unit, where the processing unit determines that the sensor signal is different from the expected sensor signal, is configured to shut down the contained system, provide a sound indication and/or visual indication that an air particle concentration is different than an expected air particle concentration, and/or interlocking access to the contained system, such as housings to the contained system, e.g. an access door to a tablet press of the contained system, and/or prevent IBCs from being undocked.

In some embodiments, the first sensor comprises an air suction means having an inlet, and wherein the monitoring system further comprises an inlet adaptor comprising one or more inlets and an outlet configured to be connected to the inlet of the first sensor, and wherein the one or more adaptor inlets are configured to allow the air suction means of the first sensor to take in air from along at least 40% of a circumference of a cross-section of the first potential leakage zone.

Thereby, the robustness of the monitoring system may be improved, as air may be taken in from a larger portion of the circumference of the circumference, so that leakages at a point along the circumference may easily be detected, notably where the potential leakage zone comprises a larger surface area, from which leakage may occur.

The one or more adaptor inlets may be configured to allow the air suction means to take in air from along at least 40% of a circumference, such as at least 50%, at least 60%, at least 70%, or at least 80% of a cross-section of the first potential leakage zone. The one or more adaptor inlet may be configured to allow a flow of air from the one or more adaptor inlets to the adaptor outlet, potentially to the inlet of the air suction means. Alternatively or additionally, the inlet adaptor may comprise a flow path for allowing air to flow from the one or more adaptor inlets to the adaptor outlet.

The first potential leakage zone may be substantially tubular and/or may have a substantially elliptical, such as a substantially circular, cross-section.

In some embodiments, the one or more adaptor inlets may be configured to direct air and/or to allow air flow towards the suction means of the first sensor. Alternatively or additionally, the one or more adaptor inlets are configured to allow the air suction means of the first sensor cause an air flow passing by at least 40% of the cross-section circumference of the first potential leakage zone, potentially so that a flow of air having passed by at least 40% of the cross-section circumference of the first potential leakage zone is taken in by the suction means of the first sensor.

Each of the one or more inlets may be in fluid connection with the outlet and, potentially, with each other. Each of the one or more inlets may be provided as openings, channels with openings, the openings potentially facing the first potential leakage zone.

In some embodiments, the inlet adaptor comprises a plurality of inlets arranged to allow the air suction means to take in air at a respective plurality of positions around the circumference of the cross-section of the first potential leakage zone, or wherein the inlet adaptor is configured to surround at least a portion of, such as at least half, the circumference of the cross-section of the first potential leakage zone.

The plurality of inlets may be and/or may comprise at least two inlets, such as at least three inlets, at least four inlets, or at least five inlets. Each of the plurality of inlets may be arranged at a respective position around the circumference of the cross-section of the first potential leakage zone. Each of the plurality of inlets may be in fluid connection with the inlet adaptor outlet. Alternatively or additionally, each of the adaptor inlets are arranged to allow a respective part of a total flow, the total flow passing through the inlet adaptor outlet to the air suction means and consisting of the respective parts of the total flow, to pass through each of the plurality of inlets.

An inlet adaptor configured to surround at least a portion of the circumference of the cross-section of the first potential leakage zone may be configured to be arranged so that an air channel is formed in between at least a portion of the inlet adaptor and the portion of the cross-section circumference. Alternatively or additionally, the inlet adaptor, where this is configured to surround at least the portion of the cross-section circumference may be configured to surround at least a portion of the potential leakage zone and/or may comprise only one inlet. The inlet adaptor may be configured to surround at least 40% such as at least 50%, such as at least 60%, such as at least 70%, such as at least 80%, of the circumference of the cross-section of the first potential leakage zone.

The inlet adaptor may be configured to allow an air crossflow across the first potential leakage zone. Alternatively or additionally, the inlet adaptor may be configured to guide particles in the air around the first potential leakage zone to the sensor.

In some embodiments, the first sensor is provided with an air suction means, such as an air suction pump.

Where any further sensor, such as a second sensor and/or a background sensor, is provided, the further sensor(s) may be provided with an air suction means, such as an air suction pump.

The air suction means may be configured to take in a predetermined volume of air from outside of the contained system.

In some embodiments, the air suction means is configured to provide an air flow of 0.5-12 l/m, preferably 1-10 l/m, preferably 2-8 l/m, preferably 2-5 l/m.

In some embodiments, the air suction means is configured to provide an air flow of around 2 l/min or around 5 l/min.

In some embodiments, the first sensor is configured to be arranged with a distance to the contained system, such as a potential leakage zone of the contained system, of 0.5-20 cm, preferably of 1-15 cm, preferably of 1-10 cm, preferably of 2-8 cm, preferably of 3-8 cm, preferably of 4-6 cm.

The distance may a distance to a specific point to the contained system, such as a desired point of measurement and/or a potential leakage zone. In some embodiments, the first sensor may be configured to be fixed to a part of the contained system, such as an exterior wall of an element of the contained system, and configured to be arranged with a distance to a desired point of measurement of 0.5-20 cm, preferably of 1-15 cm, preferably of 1-10 cm, preferably of 2-8 cm, preferably of 3-8 cm, preferably of 4-6 cm.

The distance may be determined from a point of measurement of a first sensor and/or from an air inlet of the first sensor to the contained system, such as the desired point of measurement of the contained system and/or a potential leakage zone.

The distance may be determined as the shortest distance and/or a distance along a straight line between the first sensor, such as a point of measurement or air inlet thereof, and the contained system, such as a desired point of measurement and/or a potential leakage zone thereof. Where the distance is between the first sensor and a potential leakage zone of the contained system, the distance may be the distance to a point closest within the leakage zone and/or may be to a centre point of the potential leakage zone. Alternatively or additionally, the distance may be a distance only in the horizontal direction, only in the vertical direction, or the total distance in both the horizontal direction and the vertical direction.

The first sensor may be configured to be fastened outside the contained system. The first sensor may be configured to be fastened to the contained system, such as on an exterior surface of the contained system and/or to an element thereof. The monitoring system, potentially the first sensor, may comprise a fastening element for fastening the first sensor to the contained system at the first point outside the contained system. The fastening element may be and/or may comprise one or more of an adhesive, a screw, a bracket, a clip, or a magnet. Alternatively or additionally, the fastening element may be configured to be arranged at a first point by means of a holding device, such as a stand or a holder. The fastening element may be configured to secure that the first sensor is arranged with the distance to the contained system of 0.5-20 cm, preferably of 1-15 cm, preferably of 1-10 cm, preferably of 2-8 cm, preferably of 3-8 cm, preferably of 4-6 cm and/or may be configured to aid in maintaining the distance to the contained system.

Where the monitoring system comprises a second sensor, the second sensor may be configured to be arranged with a distance to the contained system, such as a potential leakage zone of the contained system, of 0.5-20 cm, preferably of 1-15 cm, preferably of 1-10 cm, preferably of 2-8 cm, preferably of 3-8 cm, preferably of 4-6 cm.

In some embodiments, the first sensor is configured to be arranged with a distance to the contained system, wherein the distance to the contained system is based at least in part on an air flow, which the air suction means is configured to provide.

The distance to the contained system may be determined so that where an increased air flow is provided, the distance is increased. Potentially, the distance may be increased proportionally to an increase in the air flow. In some embodiments, the first sensor is configured to be arranged within a distance range to the contained system, such as the distance ranges discussed above, wherein the distance within this range is determined based on the air flow, which the suction means of the first sensor is configured to provide.

Where the monitoring system comprises a second sensor, the second sensor may be configured to be arranged with a distance to the contained system, wherein the distance to the contained system is based at least in part on an air flow, which an air suction means of the second sensor is configured to provide. The distance may be determined in a manner similar or identical to described with respect to the first sensor.

In some embodiments, the monitoring system is configured to determine a particle concentration of particles having a size within a first range, wherein the first range is a subrange within the range from 0.1-40 micrometre, preferably within the range from 0.2-25 micrometre, preferably within the range from 0.3-17 micrometre, preferably within the range from 0.5-15 micrometre, preferably within the range from 0.7-13 micrometre, preferably within the range from 1-10 micrometre.

Alternatively, in some embodiments, the monitoring system is configured to determine a particle concentration of particles having a size within a first range, wherein the first range is a subrange within the range from 0.1-300 micrometre, preferably within the range from 0.1-100 micrometre, preferably within the range from 0.1-40 micrometre, preferably within the range from 0.2-25 micrometre, preferably within the range from 0.3-18 micrometre.

Thereby, the robustness of the monitoring system may be improved, as the monitoring system may be configured to only detect particle concentrations of particles, which are emitted from the pharmaceutical component processing.

In some embodiments, the processing unit is configured to determine a particle concentration of particles having a size within the first range. The processing unit may be configured to determine the particle concentration of particles having a size within the first range based on the sensor signal from the first sensor. The processing unit may be configured to determine the particle concentration of particles having a size within the first range by filtering the sensor signal. Alternatively or additionally, the first sensor may be configured to determine a particle concentration of particles having a size within the first range, potentially by a sensor processing unit of the first sensor. Alternatively or additionally, the first sensor signal may be indicative of a particle concentration of particles having a size within the first range.

Where the monitoring system comprises a second sensor, the monitoring system may be configured to determine a particle concentration of particles having a size within a second range based on a sensor signal from the second sensor. The second range may be identical to the first range.

In some embodiments, the first sensor is configured to determine a particle concentration of particles having a size within a first range, wherein the first range is based at least in part on knowledge about the one or more pharmaceutical components of the contained system and/or based at least in part on the location of the first sensor.

Thereby the monitoring system may be configured to determine leakage of particles in the size range corresponding to the one or more pharmaceutical components, in turn providing a more robust and accurate monitoring system. For instance, where the first sensor is arranged proximal to an inlet for a particular pharmaceutical component, the first range may be the size range within some, most, or substantially all particles of the pharmaceutical component lie. Thereby, the first sensor may detect a leakage of this pharmaceutical component only, since the sensor will not detect interference from e.g. larger or smaller particles, thus improving the robustness of the monitoring system.

The knowledge about the one or more pharmaceutical components may be knowledge about the particle sizes of the any of the one or more pharmaceutical components, such as typical particle sizes and/or typical particle size ranges for a specific pharmaceutical component.

The knowledge about the location of the first sensor may be based on the first point, at which the sensor is configured to be arranged. The knowledge about the location may comprise knowledge about a potential leakage zone, for instance which pharmaceutical components passes through the potential leakage zone inside the contained system when the contained system is in operation.

In some embodiments, the first sensor is furthermore configured to provide to the processing unit a sensor signal indicative of a particle size distribution in the air outside the contained system.

In some embodiments, the first sensor is configured to provide to the processing unit a sensor signal indicative of particle concentrations in a plurality of subranges. As an example, the first sensor may be configured to provide a signal indicative of a particle count in a plurality of subranges, e.g. at least two subranges, at least four subranges, or at least eight subranges. Alternatively or additionally, the processing unit may be configured to determine a particle size distribution, such as a sensor signal indicative of a particle concentration and/or particle count, based on the sensor signal indicative of a particle size distribution in the air outside the contained system. Where the monitoring system is configured to determine a particle concentration of particles having a size within a first range, the subranges may be subranges of the first range.

Where the monitoring system comprises a further sensor, such as a second sensor and/or a background sensor, the further sensor may be configured to provide to the processing unit a further sensor signal, such as a second sensor signal and/or a background sensor signal, respectively, indicative of a particle size distribution in the air outside the contained system. The further sensor may alternatively or additionally be configured to provide to the processing unit a further sensor signal indicative of particle concentrations in a plurality of subranges, potentially identical to the plurality of subranges of the first sensor. In some embodiments, the processing unit may be configured to compare particle concentrations in the subranges determined by the first sensor and the second sensor, such as compare the particle concentration and/or count in each of the subranges from the first sensor with the particle concentration and/or count in each of the subranges from the second sensor. The processing unit may be configured to apply any arithmetic operation to the particle concentration, such as subtract a determined particle concentration based on the sensor signal from the second sensor from a determined particle concentration based on the sensor signal from the first sensor or vice versa. In some embodiments, the processing unit may be configured to compare the particle size distribution and/or the particle size concentration in one or more subranges.

In some embodiments, the monitoring system further comprises a background sensor configured to be arranged outside of the contained system and configured to repeatedly provide to the processing unit a background sensor signal indicative of a particle concentration in air outside the contained system, the background sensor being configured to be arranged with a distance to the first sensor, wherein the expected sensor signal is based at least in part on the background sensor signal.

This allows for the monitoring system to disregard any background particle concentration, i.e. concentration of particles which are not emitted from the contained system, such as dust particles in a room, in which the contained system is arranged, thereby allowing for a more robust detection of a leakage from the contained system.

The processing unit may be configured to determine a background particle concentration based on the background sensor signal. The processing unit may be configured to compare and/or subtract the background particle concentration from a particle concentration determined based on the sensor signal from the first sensor and/or based on the second sensor signal.

In some embodiments, the expected sensor signal is the background sensor signal. Alternatively or additionally, the expected sensor signal may be a threshold value, wherein the threshold value is determined based on the background sensor signal, potentially as an adaptive threshold value which is adapted repeatedly based on the background sensor signal. For instance, when the background sensor signal indicates an increase in particles, the threshold value may be increased. When the background sensor signal indicates a decrease in particle concentration, the threshold value may be decreased.

The background sensor may comprise any feature(s) described with respect to first and/or second sensor and/or may be similar or identical to the first and/or second sensor.

In some embodiments, where a second sensor is provided, the second sensor may be and/or may act as a background sensor for determining a particle concentration based on the sensor signal from the first sensor.

In some embodiments, the background sensor is configured to be arranged in connection with the contained system.

In some embodiments, the background sensor is configured to be arranged with a distance of 0.5-20 cm from a desired point of measurement.

The desired point of measurement may be a desired point of measurement in a room surrounding the contained system. Where the background sensor is and/or acts as a second sensor, the desired point of measurement may be a potential leakage zone, such as a second potential leakage zone.

In some embodiments, the background sensor is configured to be arranged with a distance of 0.5-20 cm, preferably of 1-15 cm, preferably of 1-10 cm, preferably of 2-8 cm, preferably of 3-8 cm, preferably of 4-6 cm from the desired point of measurement.

Thereby, the background sensor may be used to monitor another potential leakage zone.

In some embodiments, the background sensor is configured to provide a background sensor signal indicative of a particle concentration in intake air to a room which surrounds the contained system. In some embodiments, the monitoring system is configured to measure a particle concentration in intake air to a room which surrounds the contained system.

In some embodiments, the background sensor is configured to be arranged with a distance of 20 cm or more from the contained system.

Thereby, the background sensor may more precisely estimate the background particle concentration.

In some embodiments, the background sensor is configured to be located at the substantially same height in the vertical direction as the first sensor.

Thereby, the influence of gravity on a particle distribution, i.e. larger and heavier particles falling down to lower heights while smaller and lighter particles may be present at higher heights, may be compensated for, in turn improving the robustness of the monitoring system.

In some embodiments, the monitoring system is configured to determine a particle concentration of particles having a size within a first range, wherein the first range is based at least in part on a sensor signal from the background sensor.

The monitoring system, potentially the processing unit thereof, may determine the particle concentration based on the sensor signal from the first sensor. The processing unit and/or a sensor processing unit of the first sensor may determine the particle concentration based on the sensor signal and subsequently select, such as apply a filter, the concentration of particles having a size within the first range. Alternatively or additionally, the processing unit and/or a sensor processing unit of the first sensor may select a portion of the sensor signal and determine the concentration of particles having a size within the first range based on the portion of the sensor signal.

In some embodiments, the background sensor is configured to provide to the processing unit a sensor signal indicative of a particle size distribution.

The processing unit may be configured compare a particle size distribution determined based on the background sensor signal with a particle size distribution determined based on a respective sensor signal from the first and/or a second sensor. The processing unit may be configured to compare and/or apply arithmetic operations to these as described with respect to the first and second sensor.

The expected sensor signal may comprise a plurality of threshold values, i.e. a respective threshold value for each respective particle size subrange. For instance, when the background sensor signal indicates an increase in particles in a specific subrange of the distribution, a threshold value of the expected sensor signal for the specific subrange may be increased. When the background sensor signal indicates a decrease in particle concentration of particles having sizes within a specific subrange, the threshold value of the specific subrange may be decreased.

According to a second aspect, there is disclosed a method for monitoring performance of a contained system for processing pharmaceutical components, the contained system comprising one or more inlets for receiving one or more pharmaceutical components and one or more outlets, the method comprising the steps of:

identifying a first potential leakage zone;

arranging a first sensor outside the contained system in proximity to the first potential leakage zone, the first sensor being configured to repeatedly provide a sensor signal indicative of a particle concentration in the air; and determining a performance of the contained system based on the sensor signal, wherein the step of determining a performance of the contained system comprises comparing the sensor signal with an expected sensor signal, and where it is determined that the sensor signal is different from the expected sensor signal, outputting an output signal indicative of an air particle concentration being different than an expected air particle concentration.

The method according to the second aspect may provide identical or similar advantages to the monitoring system as described according to the first aspect of the disclosure. Notably, by arranging the first sensor outside the contained system in proximity to the first potential leakage zone, a leakage may be identified within a short time from its occurrence and appropriate actions may be taken at the detection, thus allowing for a reduced test complexity and test time as well as an improved safety of operators.

By the term "determining a performance" may be understood that it may be determined whether the contained system is sufficiently contained, i.e. whether there is a leakage or an emission of one more pharmaceutical components exceeding a certain level, such as a threshold level or the like.

The first sensor may be a first sensor of a monitoring system according to the first aspect of the invention.

A potential leakage zone may comprise one or more potential leakage points. The potential leakage zone and/or potential leakage point(s) may be as described with respect to the first aspect of the disclosure.

In some embodiments, the step of determining a performance of the contained system comprises comparing, by a processing unit operationally connectable to the first sensor, wherein the first sensor is configured to repeatedly provide to the processing unit, the sensor signal with an expected sensor signal, and where it is determined that the sensor signal is different from the expected sensor signal, outputting, by the processing unit, an output signal indicative of an air particle concentration being different than an expected air particle concentration.

In some embodiments, the contained system is arranged in a room and the step of arranging the first sensor comprises arranging the first sensor inside the room and outside the contained system.

In some embodiments of the method, the step of arranging the first sensor comprises arranging the first sensor with a distance of less than 20 cm from the first potential leakage zone.

In some embodiments, the first sensor comprises an air suction means, such as an air suction pump. In some embodiments, the step of arranging the first sensor comprises arranging the first sensor at a distance of more than 0.5 cm from the first potential leakage zone.

Potentially the step of arranging the first sensor comprises arranging the first sensor at a distance from the first potential leakage zone of more than 1 cm, such as more than 2 cm, such as more than 3 cm, such as more as 4 cm. Alternatively or additionally, the step of arranging the first sensor may comprise arranging the first sensor with a distance to the first potential leakage zone of 0.5-20 cm, such as 1-15 cm, such as 1-10 cm, such as 2-8 cm, such as 3-8 cm, such as 4-6 cm.

In some embodiments, the contained system optionally comprises a first and a second module connected at an interface, wherein the first potential leakage zone is selected from the inlet, the outlet, and, optionally, the interface.

The first and second module may each be one or more of a container, such as an intermediate bulk container, IBC, for a pharmaceutical component or for a mix thereof, a feeder, a mixer, or a tablet press.

In some embodiments, the method further comprises the step of arranging a second sensor with a distance to the first sensor of at least 10 cm, preferably at least 20 cm, preferably at least 50 cm.

In some embodiments, the method further comprises the steps of:

determining a second potential leakage zone; and arranging a second sensor in proximity with the second potential leakage zone.

The second sensor may be operationally connectable to the processing unit and may be configured to repeatedly provide to the processing unit a second sensor signal indicative of a particle concentration in the air. In some embodiments, the method may further comprise a step of determining a performance of the contained system based on the second sensor signal.

Alternatively or additionally, the step of determining a performance of the contained system based on the sensor signal may comprise determining a performance of the contained system based on the sensor signal and the second sensor signal. Potentially, the step of determining a performance of the contained system may be performed subsequent to the step of arranging the second sensor.

The second potential leakage zone may be selected from the inlet, the outlet, and, optionally, the interface. Potentially the step of arranging the second sensor comprises arranging the second sensor at a distance from the second potential leakage zone of more than 1 cm, such as more than 2 cm, such as more than 3 cm, such as more as 4 cm. Alternatively or additionally, the step of arranging the second sensor may comprise arranging the second sensor with a distance to the second potential leakage zone of 0.5-20 cm, such as 1-15 cm, such as 1-10 cm, such as 2-8 cm, such as 3-8 cm, such as 4-6 cm.

In some embodiments, the method further comprises the step of:

arranging a background sensor with a distance to the contained system of at least 20 cm, preferably at least 50 cm, preferably at least 1 m, from any potential leakage zone.

In some embodiments, the method further comprises the step of:

arranging a background sensor in proximity with an air intake of a room surrounding the contained system.

Alternatively or additionally, the step comprises arranging a background sensor with a distance to the contained system of at least 20 cm, preferably at least 50 cm, preferably at least 1 m, from any potential leakage zone and arranging the background sensor in proximity with an air intake of a room surrounding the contained system.

According to a third aspect, there is disclosed a room comprising:

a contained system for processing pharmaceutical components, the contained system comprising one or more inlets for receiving one or more pharmaceutical components and one or more outlets, and a monitoring system for monitoring performance of the contained system according to the first aspect of the invention, wherein the first sensor is arranged outside of the contained system at a first point and in the room.

The room according to the second aspect may provide identical or similar advantages to the monitoring system as described according to the first aspect of the disclosure.

The contained system of the room may be a contained system as described above with respect to the monitoring system according to the first aspect of the invention.

In some embodiments, the monitoring system may be configured to monitor performance of the contained system.

According to a fourth aspect, there is disclosed a pharmaceutical system comprising a contained system for processing pharmaceutical components, the contained system comprising one or more inlets for receiving one or more pharmaceutical components and one or more outlets, and a monitoring system for monitoring performance of a contained system according to the first aspect of the invention, wherein the first sensor is arranged outside of the contained system at a first point and in the room.

The pharmaceutical system according to the fourth aspect may provide identical or similar advantages to the monitoring system as described according to the first aspect of the disclosure.

The contained system of the pharmaceutical system may be a contained system as described above with respect to the monitoring system according to the first aspect of the invention.

In some embodiments, the monitoring system may be configured to monitor performance of the contained system.

The different aspects of the present invention can be implemented in different ways including a monitoring system for monitoring performance of a contained system, a method for monitoring for monitoring performance of a contained system, a room comprising a contained system and a monitoring system, and a system comprising a contained system and a monitoring system described above and in the following, each yielding one or more of the benefits and advantages described in connection with at least one of the aspects described above, and each having one or more preferred embodiments corresponding to the preferred embodiments described in connection with at least one of the aspects described above and/or disclosed in the dependent claims. Furthermore, it will be appreciated that embodiments described in connection with one of the aspects described herein may equally be applied to the other aspects.

BRIEF DESCRIPTION OF THE DRAWINGS

The above and/or additional objects, features, and advantages of the present invention, will be further elucidated by the following illustrative and nonlimiting detailed description of embodiments of the present invention, with reference to the appended drawings, wherein.

Similar reference numerals are used for similar elements across the various embodiments and figures described herein.

DETAILED DESCRIPTION

In the following description, reference is made to the accompanying figures, which show by way of illustration how the invention may be practiced.

Figures 1, 2:
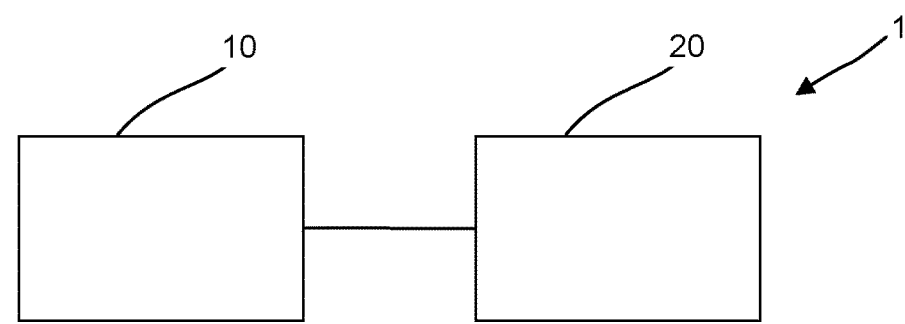
FIG. 1 shows a schematic block diagram of an embodiment of a monitoring system according to the present disclosure.
FIG. 2 shows a schematic block diagram of an embodiment of a room comprising a contained system and a monitoring system according to the present disclosure.

FIG. 1 shows a schematic block diagram of an embodiment of a monitoring system 1 according to the present disclosure. The monitoring system 1 is a monitoring system for monitoring performance of a contained system (not shown in FIG. 1) for processing pharmaceutical components, the contained system comprising one or more inlets for receiving one or more pharmaceutical components and one or more outlets. The monitoring system 1 comprises a first sensor 10 and a processing unit 20 operationally connectable to the first sensor 10. The first sensor 10 is configured to be arranged outside of the contained system at a first point. The first sensor 10 is configured to repeatedly provide to the processing unit 20 a sensor signal indicative of a particle concentration in air outside the contained system.

The processing unit 20 is configured to compare the sensor signal to an expected sensor signal.

FIG. 2 shows a schematic block diagram of an embodiment of a room R comprising a contained system 50 for processing pharmaceutical components, and a monitoring system 2 according to the present disclosure. The monitoring system 2 comprises a first sensor 10' and a processing unit 20 operationally connectable to the first sensor 10'. The first sensor 10' is configured to be arranged outside of the contained system 50 at a first point. The first sensor 10' is configured to repeatedly provide to the processing unit 20 a sensor signal indicative of a particle concentration in air outside the contained system 50.

The first sensor 10' differs from the first sensor 10 of the monitoring system 1 only in comprising a sensor processing unit 110 and an air pump 112. In other embodiments of the monitoring system 2, it will be appreciated that the first sensor 10 may be used instead of first sensor 10'.

The contained system 50 comprises a first inlet 51 for receiving one or more pharmaceutical components and an outlet 56 and an outlet 56. The contained system furthermore comprises a second inlet 52 for receiving one or more pharmaceutical components. The contained system 50 further comprises a first module 53, in the form of a mixer, and a second module 55, in the form of a tablet press, connected by an interface 54. The first 51 and second inlets 52 are each connected to the first module 53 via an interface (not shown). Additionally, the second module 55 is connected to the outlet 56 by another interface (not shown).

The first sensor 10' is arranged in proximity, such as with a distance of approximately 5 cm, to a first potential leakage zone of the contained system 50. The first potential leakage zone of the contained system is the inlet 51. The first sensor 10' comprises a sensor processing unit 100 configured to output the sensor signal indicative of the particle concentration. The sensor processing unit 100 is a central processing unit (CPU).

The monitoring system 2 further comprises a second sensor 11 operationally connectable to the processing unit 20. The second sensor 11 is arranged outside of the contained system 50 at a second point. The second point is a second potential leakage zone in the form of the interface 54. The second sensor 11 is arranged with a distance of 5 cm to the interface 54 and with a distance of more than 50 cm to the first sensor 10'. The second sensor 11 is configured to repeatedly provide to the processing unit a second sensor signal indicative of a particle concentration in air outside the contained system.

The monitoring system 2 further comprises a background sensor 12 configured to be arranged outside of the contained system 50 and configured to repeatedly provide to the processing unit 20 a background sensor signal indicative of a particle concentration in air outside the contained system 50. The background sensor 12 is arranged with a distance to the first sensor 10 and with a distance to the second sensor 11.

The processing unit 20 is configured to, where the processing unit determines that the sensor signal from at least the first sensor 10' is different from the expected sensor signal, output an output signal indicative of an air particle concentration being different than an expected air particle concentration.

The first sensor 10', the second sensor 11, and the background sensor 12 are all arranged in the room R and outside the contained system 50.

The second sensor 11 and the background sensor 12 each comprise a respective sensor processing unit 110, 120.

The processing unit 20 is arranged outside the contained system 50 in the room R surrounding the contained system 50.

The processing unit 20 is configured to compare the sensor signal to an expected sensor signal. The expected sensor signal represents and/or may be threshold value. The processing unit 20 of the monitoring system is configured to determine that a leakage has occurred when the sensor signal of the first sensor 10' and/or the sensor signal of the second sensor 11 exceeds the threshold value. The threshold is dynamically determined by the processing unit 20 based on inputs from the background sensor 12.

Each of the first sensor 10', the second sensor 11, and the background sensor 12 is provided with a respective air suction pump 102, 112, 122, each being configured to provide an air flow of 2 l/min.

The first sensor 10' and the second sensor 11 are fastened to the contained system, by means of a respective holding device (not shown).

The monitoring system is configured to determine a particle concentration of particles having a size within a first range, wherein the first range is a subrange within the range from 0.3-17 micrometre.

The processing unit 20 is configured to determine a particle concentration of particles having a size within the first range. The processing unit 20 the particle concentration of particles having a size within the first range based on the sensor signal from the first sensor 10'. The processing unit 20 the particle concentration of particles having a size within the first range based on the sensor signal from the second sensor 11.

The first sensor 10' is furthermore configured to provide to the processing unit 20 a sensor signal indicative of a particle size distribution in the air outside the contained system 50 in the form of a signal indicative of a particle count in four subranges. Similarly, the second sensor 11 and background sensor 12 are each configured to provide to the processing unit 20 a sensor signal indicative of a particle size distribution in the air outside the contained system 50 in the form of a signal indicative of a particle count in the four subranges.

The processing unit 20 is configured to compare the sensor signal to an expected sensor signal. The expected sensor signal is based at least in part on the background sensor signal.

The processing unit 20 is configured to determine a background particle concentration based on the background sensor signal. The processing unit 20 is configured to compare the background particle concentration from a particle concentration determined based on the sensor signal from the first sensor 10' and from a particle concentration determined based on the second sensor signal 11.

The background sensor 12 is configured to provide a background sensor signal indicative of a particle concentration in intake air to the room R which surrounds the contained system 50. The background sensor is arranged with a distance of 20 cm or more from the contained system 50.

Figure 3:
FIG. 3 shows a flow chart of an embodiment of a method for monitoring performance of a contained system according to the present disclosure.
Figure 3:
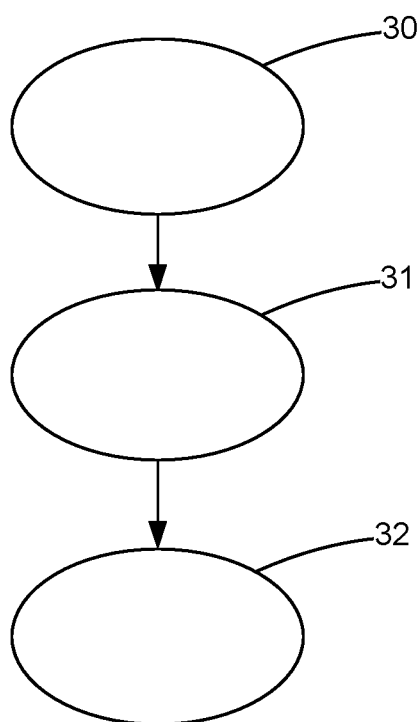

FIG. 3 shows a flow chart of an embodiment of a method 3 for monitoring performance of a contained system according to the present disclosure. The method 3 is a method for monitoring performance of a contained system for processing pharmaceutical components, the contained system comprising one or more inlets for receiving one or more pharmaceutical components and one or more outlets. The method 3 comprises the steps of:

identifying 30 a first potential leakage zone;
  arranging 31 a first sensor outside the contained system in proximity to the first potential leakage zone, the first sensor being configured to repeatedly provide a sensor signal indicative of a particle concentration in the air; and
  determining 32 a performance of the contained system based on the sensor signal.

Figure 4:
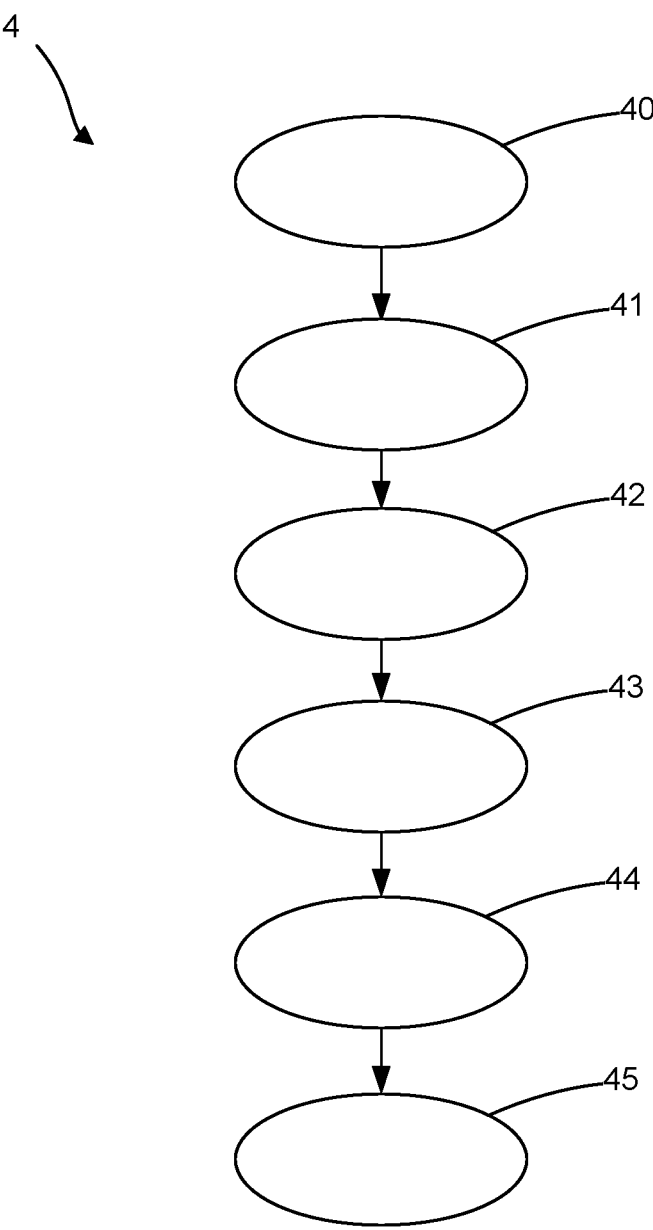
FIG. 4 shows a flow chart of an embodiment of a method for monitoring performance of a contained system according to the present disclosure.

FIG. 4 shows a flow chart of an embodiment 4 of a method for monitoring performance of a contained system according to the present disclosure. The method 4 comprises the steps of identifying 40 a first potential leakage zone;
  arranging 41 a first sensor outside the contained system in proximity to the first potential leakage zone, the first sensor being configured to repeatedly provide a sensor signal indicative of a particle concentration in the air; and The steps of identifying 40 and arranging 41 are similar to the steps 30 and 31 of method 3.

In the method 4, the contained system is arranged in a room. The step of arranging 41 the first sensor comprises arranging the first sensor inside the room and outside the contained system. The step of arranging 41 the first sensor comprises arranging the first sensor with a distance of less than 20 cm, such as approximately 5 cm from the first potential leakage zone.

The first sensor comprises an air suction means, such as an air suction pump, and the step of arranging 41 the first sensor further comprises arranging the first sensor at a distance of more than 0.5 cm from the first potential leakage zone.

The contained system optionally comprises a first and a second module connected at an interface, wherein the first potential leakage zone is selected from the one or more inlets, the one or more outlets, and, optionally, the interface. The step of identifying 40 the first potential leakage zone comprises selecting the first potential leakage zone from the one or more inlets, the one or more outlets, and, optionally, the interface.

The method 4 further comprises the steps of:
determining 42 a second potential leakage zone; and
arranging 43 a second sensor in proximity with the second potential leakage zone.

The step of arranging 43 the second sensor further comprises arranging the second sensor with a distance to the first sensor of at least 10 cm, such as at least 20 cm, such as at least 50 cm.

The second sensor is operationally connectable to the processing unit and is configured to repeatedly provide to the processing unit a second sensor signal indicative of a particle concentration in the air.

The method 4 further comprises the step of:
arranging 44 a background sensor with a distance to the contained system of at least 20 cm, preferably at least 50 cm, preferably at least 1 m, from any potential leakage zone. In the method 4, the step of arranging the background sensor 44 comprises arranging the background sensor in proximity with an air intake of a room surrounding the contained system.

The method 4 moreover comprises the step of determining 45 a performance of the contained system based on the sensor signal from the first sensor and the second sensor signal.

Figure 5A:
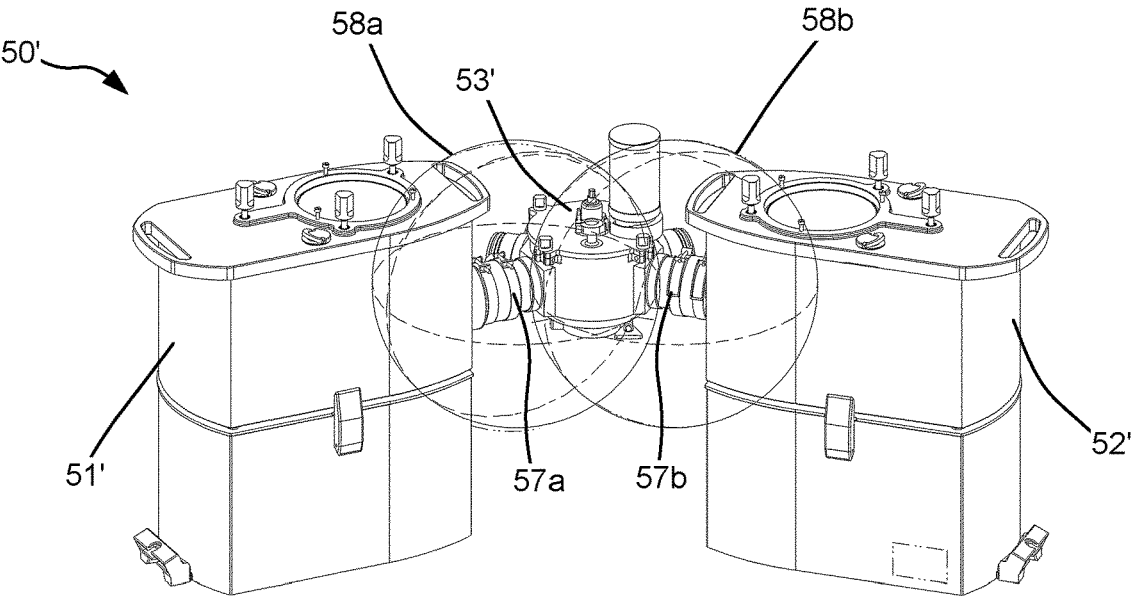
FIG. 5a shows a perspective view of elements of a contained system.
Figure 5B:
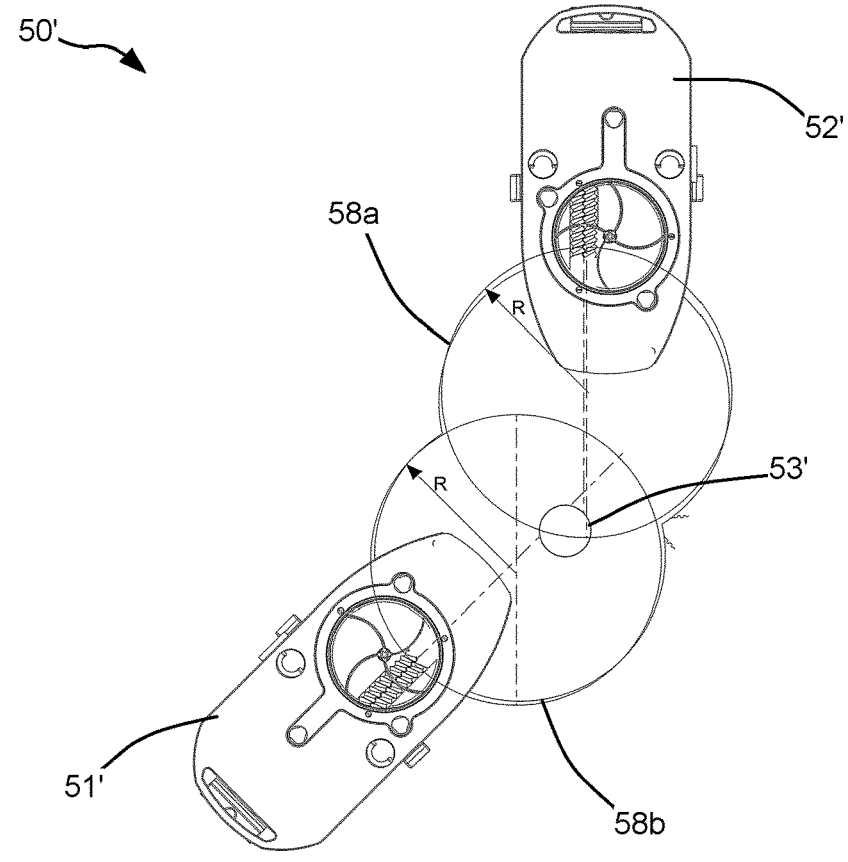
FIG. 5b shows a top-down cross-sectional view of elements of the contained system shown in FIG. 5a, FIG. 6a shows a perspective view of elements of a contained system.

FIG. 5a shows a perspective view of elements of a contained system 50', whereas FIG. 5b shows a top-down cross-sectional view of elements of the contained system 50'. The contained system 50' comprises a first container, a first IBC 51', for a pharmaceutical component and a second container, a second IBC 52', for another pharmaceutical component. The first 51' and second IBC 52' are both connected to a mixer 53' by means of a respectable first substantially tubular interface 57a and a second substantially tubular interface 57b. Each of the first substantially tubular interface 57a and a second substantially tubular interface 57b comprise potential leakage zones.

As shown in FIGS. 5a and 5b, a first sphere 58a indicates a distance R of 20 cm from a centre point of the first substantially tubular interface 57a is indicated, i.e. a distance of 20 cm from a potential leakage point of a first potential leakage zone constituted by the first substantially tubular interface 57a. The second sphere 58b indicates a distance R of 20 cm from a centre point of the first substantially tubular interface 57b is indicated, i.e. a distance of 20 cm from a potential leakage point of a second potential leakage zone constituted by the first substantially tubular interface 57b. The first sphere 58a and the contained system 50' delimits a volume within which a first sensor of a monitoring system (not shown in FIGS. 5a-5b) may advantageously be arranged. The volume has a substantially spherical outer periphery. The second sphere 58a and the contained system 50' delimits a volume within which a potential second sensor of a monitoring system (not shown in FIGS. 5a-5b) may advantageously be arranged. The volume has a substantially spherical outer periphery. In other embodiments, a volume in which a potential second sensor of a monitoring system may advantageously be arranged may have a distance of 20 cm from any point of a volume outer periphery to a respective nearest point of the potential leakage zone. For instance, where the potential leakage zone is tubular, the volume may have a substantially cylindrical outer periphery portion and two half-sphere portions at each end of the substantially cylindrical outer periphery portion.

Figure 6A:
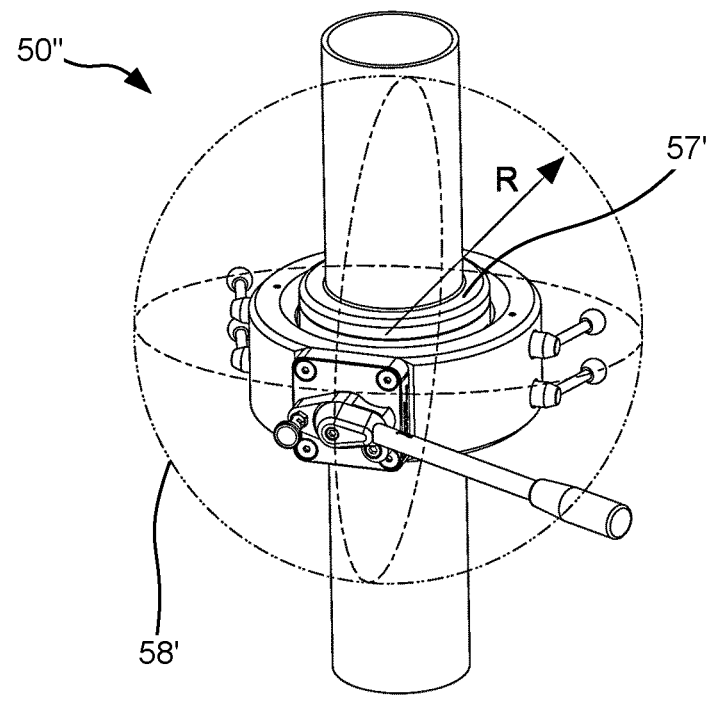
FIG. 6b shows a cross-sectional view of elements of the contained system shown in FIG. 6a, FIG. 7 shows a schematic view of an inlet adaptor element of an embodiment of a monitoring system according to the present disclosure.
Figure 6B:
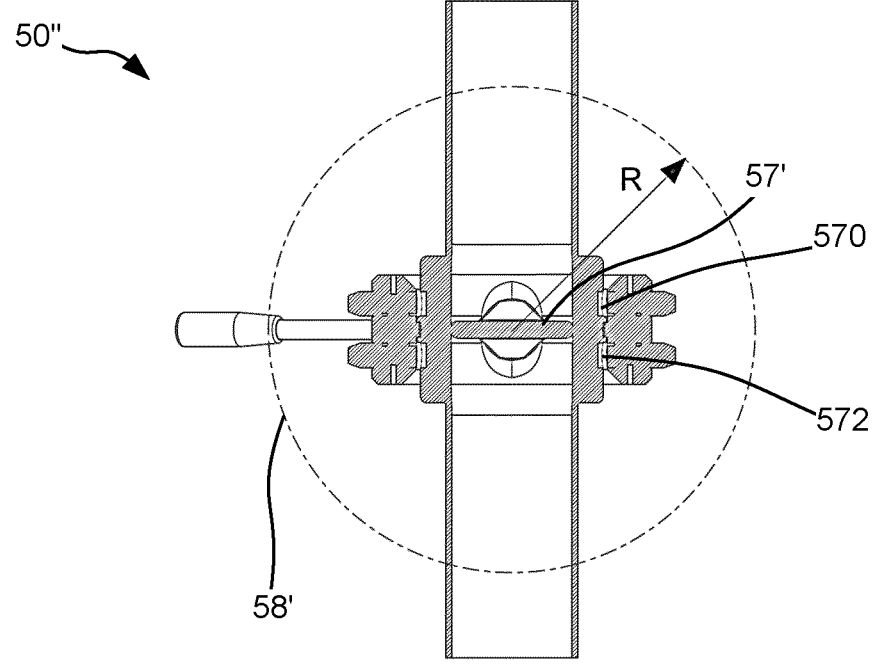

FIG. 6a shows a perspective view of elements of a contained system 50", whereas FIG. 6b shows a cross-sectional view of elements of the contained system 50" shown in FIG. 6a.

In FIGS. 6a and 6b, two tubes connected by means of a two-section split butterfly valve 57', which can be opened and closed are shown. The valve 57' constitutes a potential leakage zone.

On FIGS. 6a and 6b a sphere 58' indicates a distance R of 20 cm from a centre point of the potential leakage zone, i.e. the valve 57'. Similar to the spheres shown with respect to the contained system elements of FIGS. 5a and 5b, the sphere 58' and the contained system 50" here delimits an air volume outside of the contained system within which a sensor of a monitoring system may advantageously be arranged. While, in FIGS. 6a and 6b, the volume defined by the sphere 58' is spherical, i.e. has a globular outer periphery, the volume may in other embodiments have a periphery having a substantially tubular section. Alternatively or additionally, each point on the periphery of the volume may have a distance of 20 cm to a respective nearest point of the potential leakage zone 57'.

The potential leakage zone of the valve 57' comprises a first potential leakage sub-zone 570 and a second potential leakage sub-zone 572, each comprising a plurality of potential leakage points. The first 570 and second potential leakage sub-zones extend along the valve 57' around the tubes. In some embodiments, the volume is defined so that each point on its periphery has a distance of 20 cm to a nearest potential leakage point of the first 570 and second potential leakage points 572.

Figure 7:
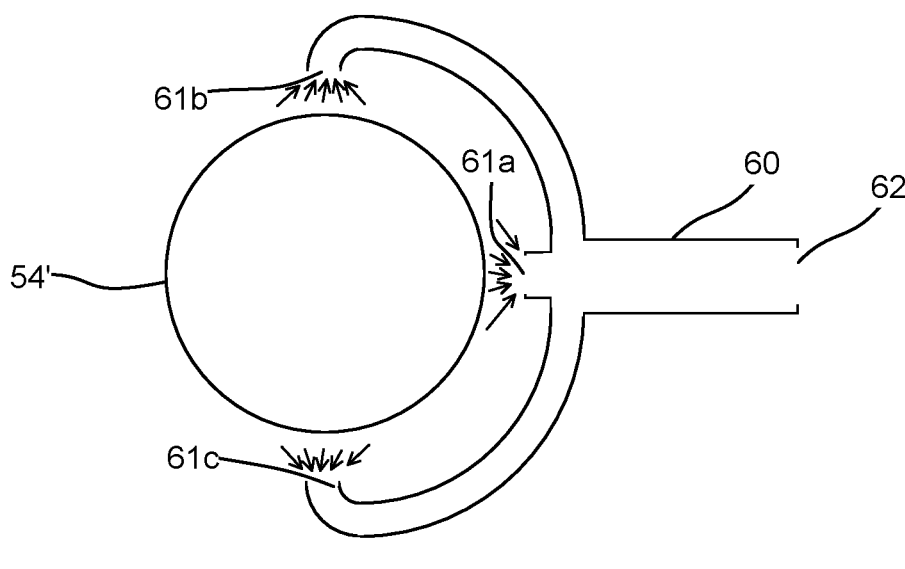

FIG. 7 shows a schematic view of an inlet adaptor element 60 of an embodiment of a monitoring system according to the present disclosure.

The inlet adaptor 60 comprises three inlets 61a, 61b, and 61c and an outlet 62. The outlet 62 is configured to be connected to an inlet of the first sensor (not shown in FIG. 7). The adaptor inlets 61a, 61b, and 61c are configured to allow the air suction means of the first sensor to take in air from along at least 40% of a circumference of a cross-section of the first potential leakage zone 54'. Air flows are indicated by arrows of FIG. 7.

The first potential leakage zone 54' is an interface of a first module and a second module of a contained system (not shown in FIG. 7).

The three inlets 61a, 61b, and 61c are each in fluid connection with the outlet 62 and with each other. Each of the adaptor inlets 61a, 61b, and 61c are provided as channels with openings. Each of the openings are facing the first potential leakage zone 54'.

The adaptor inlets 61a, 61b, and 61c are configured to allow the air suction means to take in air from along at least 50% of a circumference of a cross-section of the first potential leakage zone 54'. The adaptor inlets 61a, 61b, and 61*c* are configured to allow a flow of air from the one or more adaptor inlets to the adaptor outlet 62.

The first potential leakage zone 54' is substantially tubular and has a substantially circular cross-section.

The adaptor inlets 61*a*, 61*b*, and 61*c* are configured to allow the air suction means of the first sensor cause an air flow passing by at least 50% of the cross-section circumference of the first potential leakage zone 54'.

The inlet adaptor inlets 61*a*, 61*b*, and 61*c* are arranged to allow the air suction means to take in air at three respective positions around the circumference of the cross-section of the first potential leakage zone 54'.

Figure 8:
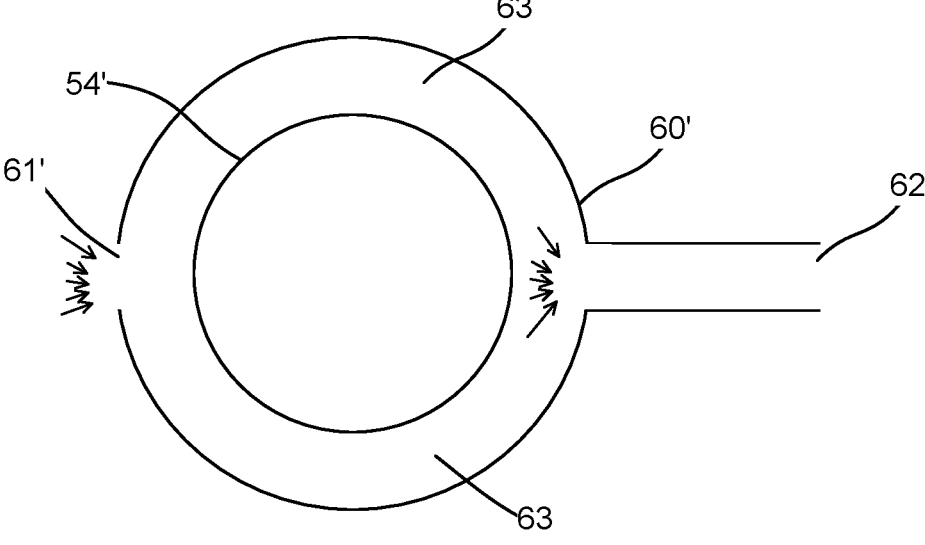
FIG. 8 shows a schematic view of an inlet adaptor element of an embodiment of a monitoring system according to the present disclosure.

FIG. 8 shows a schematic view of an inlet adaptor element of an embodiment of a monitoring system according to the present disclosure.

FIG. 8 shows a schematic view of an inlet adaptor element 60' of an embodiment of a monitoring system according to the present disclosure.

The inlet adaptor 60' comprises one inlet 61' and an outlet 62. The outlet 62 is configured to be connected to an inlet of the first sensor (not shown in FIG. 8). The adaptor inlet 61' is configured to allow the air suction means of the first sensor to take in air from at least 40% of a circumference of a cross-section of the first potential leakage zone 54'. An air flow is indicated by arrows of FIG. 8.

The first potential leakage zone 54' is an interface of a first module and a second module of a contained system (not shown in FIG. 8).

The inlet 61' is in fluid connection with the outlet 62. The inlet 61' is provided as an opening in the inlet adaptor element 61' towards the surroundings.

The inlet adaptor 60' is configured to surround at least 60% of the circumference of the cross-section of the first potential leakage zone 54'.

The 60' inlet adaptor configured to surround at least a portion of the circumference of the cross-section of the first potential leakage zone 54' is arranged so that an air channel 63 is formed in between a portion of the inlet adaptor 60' and a portion of the cross-section circumference of the potential leakage zone 54'. The inlet adaptor 60' comprises only one inlet 61'.

The adaptor inlet 61' is configured to allow a flow of air from the one or more adaptor inlets to the adaptor outlet 62. The adaptor inlet 61' is configured to allow the air suction means of the first sensor cause an air flow passing by at least 60% of the cross-section circumference of the first potential leakage zone 54', so that a flow of air having passed by at least 60% of the cross-section circumference of the first potential leakage zone 54' is present at the outlet 62.

Although some embodiments have been described and shown in detail, the invention is not restricted to them, but may also be embodied in other ways within the scope of the subject matter defined in the following claims. In particular, it is to be understood that other embodiments may be utilised, and structural and functional modifications may be made without departing from the scope of the present invention.

In device claims enumerating several means, several of these means can be embodied by one and the same item of hardware. The mere fact that certain measures are recited in mutually different dependent claims or described in different embodiments does not indicate that a combination of these measures cannot be used to advantage.

It should be emphasized that the term "comprises/comprising" when used in this specification is taken to specify the presence of stated features, integers, steps or components but does not preclude the presence or addition of one or more other features, integers, steps, components or groups thereof.

What is claimed is:

1. A monitoring system for monitoring performance of a contained system for processing pharmaceutical components, the contained system comprising one or more inlets for receiving one or more pharmaceutical components and one or more outlets, the monitoring system comprising a first sensor and a processing unit operationally connectable to the first sensor, wherein the first sensor is configured to be arranged outside of the contained system at a first point, and the first sensor is configured to repeatedly provide to the processing unit a sensor signal indicative of a particle concentration of particles from the one or more pharmaceutical components having a size larger than 0.1 micrometre in air outside the contained system, wherein the processing unit is configured to compare the sensor signal with an expected sensor signal, and wherein the processing unit, where the processing unit determines that the sensor signal is different from the expected sensor signal, is configured to output an output signal indicative of an air particle concentration being different than an expected air particle concentration to indicate a containment breach of the contained system.

2. The monitoring system according to claim 1, wherein the first sensor is configured to be arranged in proximity to a first potential leakage zone of the contained system.

3. The monitoring system according to claim 2, wherein the first sensor comprises an air suction means having an inlet, and wherein the monitoring system further comprises an inlet adaptor comprising one or more inlets and an outlet configured to be connected to the inlet of the first sensor, and wherein the one or more adaptor inlets are configured to allow the air suction means of the first sensor to take in air from along at least 40% of a circumference of a cross-section of the first potential leakage zone.

4. The monitoring system according to claim 3, wherein inlet adaptor comprises a plurality of inlets arranged to allow the air suction means to take in air at a respective plurality of positions around the circumference of the cross-section of the first potential leakage zone, or wherein the inlet adaptor is configured to surround at least a portion of the circumference of the cross-section of the first potential leakage zone.

5. The monitoring system according to claim 1, wherein the first sensor is configured to be arranged with a distance to the contained system of 0.5-20 cm.

6. The monitoring system according to claim 1, wherein the monitoring system is configured to determine a particle concentration of particles having a size within a first range, wherein the first range is a subrange within the range from 0.1-300 micrometre.

7. The monitoring system according to claim 1, wherein the monitoring system is configured to determine a particle concentration of particles having a size within a first range, wherein the first range is based at least in part on one or more of knowledge about the one or more pharmaceutical components of the contained system or the location of the first sensor.

8. The monitoring system according to claim 1, wherein the first sensor is furthermore configured to provide to the processing unit a sensor signal indicative of a particle size distribution in the air outside the contained system.

9. The monitoring system according to claim 1, further comprising a background sensor configured to be arranged outside of the contained system and configured to repeatedly provide to the processing unit a background sensor signal indicative of a particle concentration in air outside the contained system, the background sensor being configured to be arranged with a distance to the first sensor, wherein the expected sensor signal is based at least in part on the background sensor signal.

10. The monitoring system according to claim 1, wherein the first sensor is configured to be arranged with a distance to the contained system of 2-8 cm.

11. The monitoring system according to claim 1, wherein the first sensor is configured to be arranged with a distance to the contained system of 4-6 cm.

12. The monitoring system according to claim 1, wherein the monitoring system is configured to determine a particle concentration of particles having a size within a first range, wherein the first range is a subrange within the range from 0.1-40 micrometre.

13. The monitoring system according to claim 1, wherein the monitoring system is configured to determine a particle concentration of particles having a size within a first range, wherein the first range is a subrange within the range from 0.3-18 micrometre.

14. A method for monitoring performance of a contained system for processing pharmaceutical components, the contained system comprising one or more inlets for receiving one or more pharmaceutical components and one or more outlets, the method comprising:

identifying a first potential leakage zone;

arranging a first sensor outside the contained system in proximity to the first potential leakage zone, the first sensor being configured to repeatedly provide a sensor signal indicative of a particle concentration in the air of particles from the one or more pharmaceutical components; and determining a performance of the contained system based on the sensor signal, wherein the step of determining a performance of the contained system comprises comparing the sensor signal with an expected sensor signal, and where it is determined that the sensor signal is different from the expected sensor signal, outputting an output signal indicative of an air particle concentration being different than an expected air particle concentration to indicate a containment breach of the contained system.

15. The method according to claim 14, wherein the contained system is arranged in a room and wherein arranging the first sensor comprises arranging the first sensor inside the room and outside the contained system.

16. The method according to claim 14, wherein arranging the first sensor comprises arranging the first sensor with a distance of less than 20 cm from the first potential leakage zone.

17. The method according to claim 14, wherein the contained system comprises a first and a second module connected at an interface, wherein the first potential leakage zone is selected from the one or more inlets, the one or more outlets, and the interface.

18. The method according to claim 14, further comprising:

arranging a background sensor with a distance to the contained system of at least 20 cm, from any potential leakage zone.

19. The method according to claim 14, further comprising:

arranging a background sensor with a distance to the contained system of at least 1 m, from any potential leakage zone.

20. A room comprising:

a contained system for processing pharmaceutical components, the contained system comprising one or more inlets for receiving one or more pharmaceutical components and one or more outlets, and a monitoring system for monitoring performance of the contained system, the monitoring system comprising a first sensor and a processing unit operationally connectable to the first sensor, wherein the first sensor is configured to be arranged outside of the contained system at a first point, and the first sensor is configured to repeatedly provide to the processing unit a sensor signal indicative of a particle concentration of particles from the one or more pharmaceutical components having a size larger than 0.1 micrometre in air outside the contained system, wherein the processing unit is configured to compare the sensor signal with an expected sensor signal, and wherein the processing unit, where the processing unit determines that the sensor signal is different from the expected sensor signal, is configured to output an output signal indicative of an air particle concentration being different than an expected air particle concentration to indicate a containment breach of the contained system.

* * * * *